Figure 1:
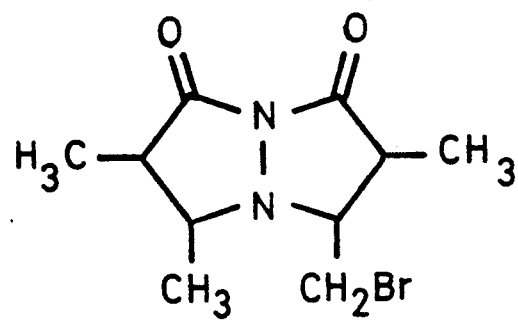
Figure 1:
Figure 1:
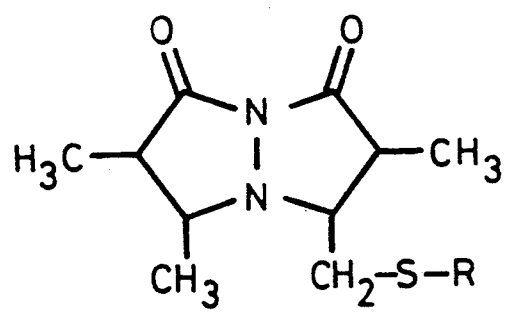

United States Patent [19]
Jackson

[11] Patent Number: 5,320,727
[45] Date of Patent: Jun. 14, 1994

[54] ELECTROPHORESIS

[75] Inventor: Peter Jackson, Cambridge, Great Britain

[73] Assignee: Astromed Limited, Cambridge, England

[21] Appl. No.: 94,169

[22] PCT Filed: Feb. 12, 1992

[86] PCT No.: PCT/GB92/00249
§ 371 Date: Jul. 27, 1993
§ 102(e) Date: Jul. 27, 1993

[87] PCT Pub. No.: WO92/14747
PCT Pub. Date: Sep. 3, 1992

[30] Foreign Application Priority Data

Feb. 13, 1991 [GB] United Kingdom ............... 9103073

[51] Int. Cl.$^5$ .................. G01N 27/26; G01N 27/447
[52] U.S. Cl. .............................. 204/182.1; 204/182.9; 204/182.8; 204/180.1
[58] Field of Search ............... 204/182.9, 182.8, 180.1, 204/182.1

[56] References Cited

PUBLICATIONS

Egil Jellum et al "Capillary Electrophoresis for Diagnosis and Studies of Human Disease, Particularly Metabolic Disorders" Journal of Chromatography, 559 (1991) 455-465.

Barry L. Hogan and Edward S. Yeung "Determination of Intracellular Species at the Level of a Single Erythrocyte via Capillary Electrophoresis with Direct and Indirect Fluorescence Detection".

Nechama S. Kosower et al "Bimane Fluorescent Labels, Characterization of the Bimane Labeling of Human Hemoglobin" Biochimica et Biophysica Acta 622 (1980) 201-209.

Nechama S. Kosower et al "Dynamic Changes of Red Cell Membrane Thiol Groups Followed by Bimane Fluorescent Labelling" Biochimica et Biophysica Acta, 640 (1981) 748-759.

Arduino Arduini and Arnold Stern "Spectrin Degradation In Intact Red Blood Cells by Phenylhydrazine" Biochemical Pharmacology, vol. 34, No. 24 (1985) 4283-4289.

G. E. Neal et al "Conjugation of Model Substrates of Microsomally-Activated Aflatoxin B, with Reduced Glutathione, Catalyzed by Cytosolic Glutathione-S-Transferases In Livers of Rats, Mice, and Guinea Pigs" Biochemical Pharmacology, vol. 36, No. 24 (1987) 4269-4276.

Kalomiris, "Thiol-specific probes indicate that the beta-chain of platelet ... (etc.)", Biochemistry, vol. 24, No. 20, Sep. 24, 1985, pp. 5430-5436.

Kosower, "Bimane fluorescent labels characterization of the bimane labeling of human hemoglobin", Chemical Abstracts, vol. 93, No. 5, Aug. 4, 1980.

Cornwall, "Characterization of sulphydryl proteins involved in the maintenance of flagellar . . . (etc.)", Medline on line abstracts, abstract No. 90216425.

Primary Examiner—John Niebling
Assistant Examiner—John S. Starsiak, Jr.
Attorney, Agent, or Firm—Lee, Mann, Smith, McWilliams, Sweeney & Ohlson

[57] ABSTRACT

A method of separating or distinguishing proteins by isoelectric focusing (IEF), comprises fluorescently labelling proteins by reacting monobromobimane or monochlorobimane with free sylphydryl groups of proteins, and subjecting the labelled proteins to isoelectric focusing. The IEF may be followed by a second electrophoretic separation step, resulting in 2-D electrophoresis of flourescently pre-labelled proteins in a way that has not hitherto been possible.

11 Claims, 2 Drawing Sheets

+

SH—R

↓

+
HBr

+

SH — R

+
HBr

ELECTROPHORESIS

FIELD OF THE INVENTION

This invention relates to electrophoresis.

BACKGROUND TO THE INVENTION

Electrophoresis is a well known separation technique which separates charged units on the basis of differential mobility in an electric field (which depends on the size, shape and charge of the units), and is widely used for separation of proteins and other materials. A variant of electrophoresis known as isoelectric focusing (IEF) exploits the fact that the net charge on a protein molecule varies with the pH of the surrounding solution. At a pH that is characteristic for each protein there exists an isoelectric point (IEP) at which the protein has no net charge and therefore will not migrate in an electric field. In IEF, electrophoresis is carried out in a pH gradient established by use of buffer mixtures, commonly using carrier ampholytes, and each protein migrates to the position in the gradient that corresponds to its isoelectric point and then remains there.

Two dimensional (2D) electrophoresis techniques are also known, involving a first electrophoretic separation in a first dimension, followed by a second electrophoretic separation in a second, transverse dimension. The 2D method most commonly used is that based on the work of O'Farrell (reference 1) in which proteins are subjected to IEF in a polyacrylamide gel in the first dimension, resulting in separation on the basis of isoelectric point, and are then subjected to polyacrylamide gel electrophoresis in the second dimension in the presence of sodium dodecyl sulphate (SDS), resulting in further separation on the basis of size.

Two dimensional polyacrylamide gel electrophoresis (2D-PAGE) is at present the most highly resolving method for the analysis of protein mixtures. Using this technique it is possible to separate several thousand individual polypeptide chains from a single sample in a single electrophoretic analysis. Methods which enable this are well established, used widely and all of the necessary equipment and reagents can be obtained readily from commercial sources.

Proteins are detected usually by staining either by a dye, which is most commonly Coomassie Brilliant Blue R-250 (C.I. 42660), or by deposition of metallic silver. Alternatively proteins which have been radiolabelled before analysis either in vivo or in vitro, for instance by reductive methylation (reference 2), can be detected by autoradiography or fluorography. The radiolabelling method is the only one which is at present available in which proteins can be labelled before analysis by 2D-PAGE in which IEF is used as the first dimension.

Fluorophores have also been used to label proteins both before and after PAGE. Several papers have described prelabelling methods for 1D-PAGE (reference 3). The advantages of pre- over post-electrophoretic labelling are the possibility of viewing the separation during the electrophoresis, the ease of detecting the results at the end without further processing of the gel, the ease of viewing gels of various sizes and thickness, the avoidance of problems associated with handling delicate gels, the avoidance of losing small molecules from the gel during staining, the high sensitivity which can be achieved, and the avoidance of use of radioactive materials.

Recently the fluorophore labelling of proteins present in IEF gels has been described which enabled the subsequent generation of a fluorescent 2D-electrophoretogram. The method allows normal IEF to be combined with the advantages of pre-electrophoretic fluorescent labelling (reference 4).

Another recent paper (reference 5) describes in vivo monitoring of protein sulphydryl (SH) groups of hamster spermatazoa by labelling with the fluorescent material monobromobimane and 2-D electrophoretic analysis. The first dimension uses non-equilibrium pH gradient electrophoresis (NEPHGE), followed by SDS-PAGE in the second dimension. In NEPHGE a pH gradient is generated but proteins are loaded at the acidic end of the gel, are positively charged and do not reach their IEPs. The method is used for analysing proteins with basic IEPs which cannot be analysed by IEF because of the difficulty in obtaining stable pH gradients at alkaline pHs.

Hitherto, no method has been demonstrated which enables useful separations to be obtained after the pre-IEF labelling of proteins with either fluorophores or chromophores. So far no protein derivatization with a fluorophore or chromophore has been demonstrated in which the charge properties (ie pK) of the derivative exactly mimics that of the underivatized protein. Thus, derivatization with such reagents causes changes in the IEPs of the proteins, which leads to the IEF pattern being altered. The reason for this is two fold. It can be difficult to ensure 100% modification of the protein. Partial modification will lead to the focusing at different IEPs of each species of each individual polypeptide carrying a different percentage of modification. Indeed, this property of partially modified proteins has been used to generate a "charge-train", by carbamylation of lysine residues by cyanate. Such charge modifications can be used as a standard for IEF (eg Carbamylyte (Pharmacia-LKB)). Moreover, if 100% modification of one type of reactive residue (eg lysine) is obtained and the charge on it altered then the protein will focus with a new IEP and thus the pattern of separation will be either quite different from that obtained with unmodified protein or it may be impossible to obtain a useful separation pattern (eg if the protein becomes very acidic).

The present invention is based on a novel approach to labelling of proteins for separation by IEF, which enables separating by IEF of fluorescently pre-labelled proteins.

SUMMARY OF THE INVENTION

In its broadest aspect the present invention provides a method of separating or distinguishing proteins by isoelectric focusing, comprising fluorescently labelling proteins by reacting monobromobimane or monochlorobimane with free sulphydryl groups of the proteins, and subjecting the labelled proteins to isolelectric focusing.

It is found that by using these particular label materials free sulphydryl groups in proteins can be covalently derivatised by a reactive fluorophore before IEF in a way which does not affect significantly the IEPs of the proteins. IEF separation patterns for labelled and unlabelled proteins are thus almost identical. Further, separations of labelled and untreated proteins are similar in most cases when using 1D-SDS-PAGE. The invention thus enables fluorescently labelled proteins to be analysed by IEF in a way which has not hither to been possible, with obvious advantages.

The IEF may be followed by a second electrophoretic separation step, resulting in 2-D electrophoresis of fluorescently pre-labelled proteins in a way which has not hitherto been possible. The second dimension separation is preferably carried out in the presence of SDS.

Hence, in a preferred aspect the present invention provides a method of separating or distinguishing proteins by two dimensional electrophoresis, comprising fluorescently labelling proteins by reacting monobromobimane or monochlorobimane with free sulphydryl groups of the proteins, subjecting the labelled proteins to isoelectric focusing in a first dimension, then subjecting the proteins to sodium dodecyl sulphate gel electrophoresis in a second dimension.

Monobromobimane (also known by the abbreviation TMB) and monochlorobimane (also known by the the abbreviation TMC) are commercially available from Calbiochem under the trade names Thiolyte MB and Thiolyte MC, respectively. These reagents are also available from other suppliers, eg Molecular Probes. The structure of monobromobimane and its reaction with the free sulphydryl group of a protein to produce a fluorescent derivative are shown in FIG. 1, where R is the remainder of a protein molecule.

Labelling is conveniently effected by reacting protein in lysis buffer with monobromobimane or monochlorobimane added in solution in acetonitrile, by mixing and incubating at room temperature for between 2-60 minutes, eg 10 minutes, which results in production of a highly fluorescent derivative. The derivatives show absorption maxima at 370 to 385 nm and emit light at 477 to 484 nm. The fluorescence quantum yields are in the range 0.1 to 0.3.

Some proteins include free sulphydryl groups, and can be reacted directly with the label material. Generally, however, free sulphydryl groups are produced by reduction in known manner of disulphide bridges (cystinyl residues). Reducing agents such as dithioerythritol (DTE), dithiothreitol (DTT), 2-mercaptoethanol or tributylphosphine are conveniently used for this purpose.

The electrophoretic separations are conveniently carried out on polyacrylamide gels using known techniques, eg generally as described in reference 1.

The resulting patterns of fluorescent bands or spots can be viewed when suitably illuminated, eg using an ultra violet light box with suitable filter. However, best results are obtained by viewing gels using an imaging system based on a cooled 2D charge coupled device (CCD), such as the Astromed 22000 imaging system. Viewing techniques are described in reference 4.

Very good results have been obtained using monobromobimane as the label, and it is expected that similar result will be obtained with monochlorobimane.

The method of the invention has been used to generate high resolution 2D-spot patterns which are almost identical to those obtained with standard post-electrophoresis silver staining. The fluorescent electrophoretograms have been viewed using an imaging system based on a cooled CCD without removing the gels from their glass molds and with a sensitivity similar to or greater than that obtained using silver staining.

Figure 2:
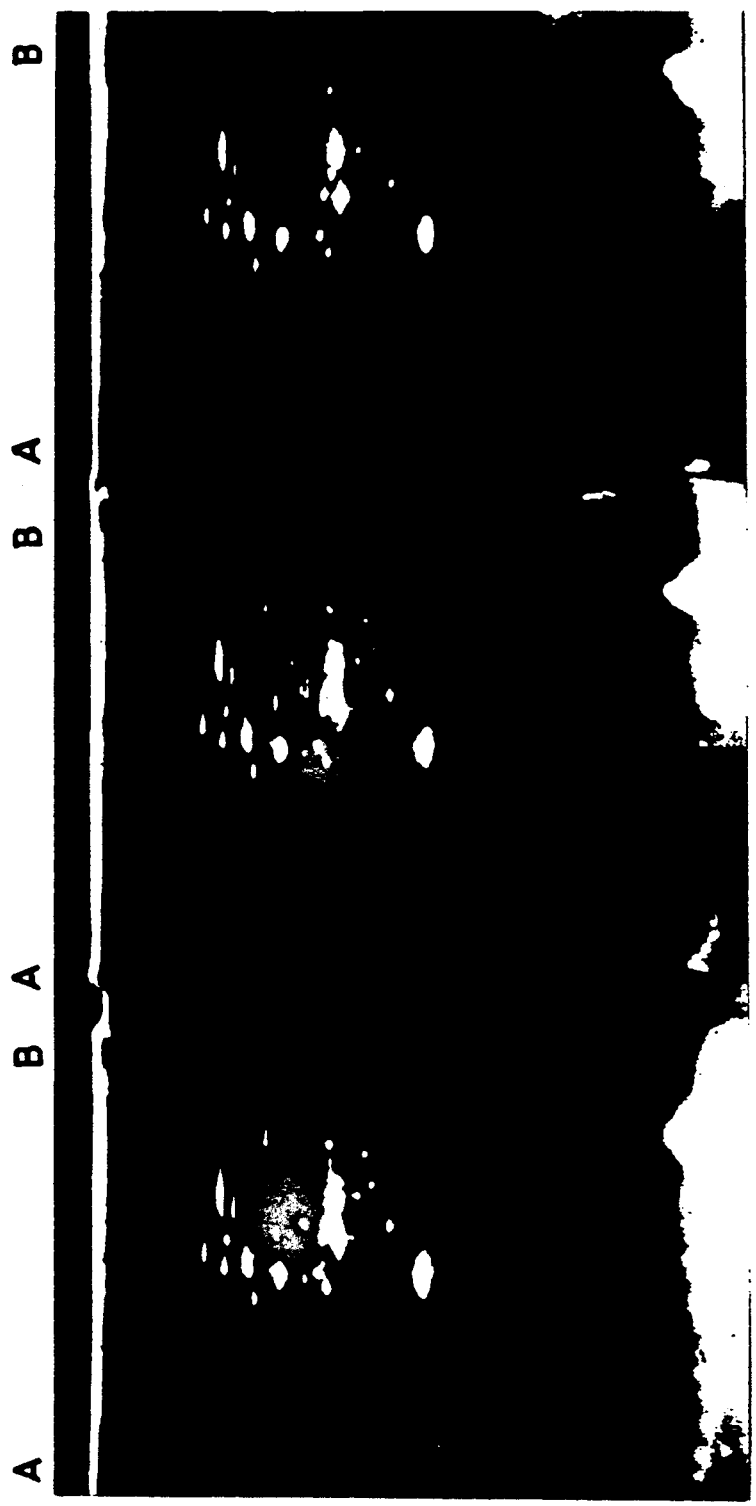

The invention is further illustrated in the following non-limiting Example and by reference to the accompanying Figures, in which:

FIG. 1 illustrates the structure of monobromobimane and its reaction with the free sulphydryl group of a protein; and FIG. 2 is a photograph of a 2D electrophoretic gel produced using the method of the invention.

EXAMPLE 2D electrophoresis of proteins obtained from the bacterium Neisseria gonorrhoeae was carried out by the method of the invention, using monobromobimane as the label.

In outline, proteins were dissolved in a denaturing solution (comprising urea and the detergent Nonidet P40 (NP40) (Shell Chemical Co)) and also containing a reducing agent (dithioerythritol (DTE) (Sigma)) which converts all disulphide bridges (cystinyl residues) to free sulphydryl groups. Monobromobimane (TMB from Calbiochem) in solution in acetonitrile was added to the protein solution where it reacts covalently with free sulphydryl groups, alkylating them, as illustrated in FIG. 1, and generating a highly fluorescent label. The labelled proteins are subjected to 2D-PAGE, generally as described in reference 1, generating a fluorescent spot pattern which is similar to that obtained without pre-labelling and using silver staining for detection.

MATERIALS AND METHODS

Proteins and reagents

The bacterium Neisseria gonorrhoeae strain OR9, was grown in bulk at the Public Health Laboratory Centre for Applied Microbiology and Research (Porton, Wiltshire, U.K.) as described previously (reference 6). It was harvested in late log-phase after approximately 9h growth. The bacteria were washed, suspended in $H_2H$ and disrupted by ultra sound. The soluble proteins were obtained in the supernatant after centrifugation at 65000 g for 15 minutes at $+4°$ C. The protein concentration was 50 mg/ml as determined by the dye binding method of Bradford (reference 7) and using bovine plasma gamma globulin (Biorad) as standard.

A small aliquot (1.0 ul) of supernatant was diluted in 300 ul of lysis buffer containing 9M urea, 10 mM dithioerythritol (DTE), 2% v/v carrier ampholytes, pH range 3-10 (LKB), 4% v/v Nonidet P40 (NP40). The mixture was then mixed vigorously for 1 minute, centrifuged at 10000 g for 2 minutes at $+4°$ C.

A stock solution of 200 mM monobromobimane in acetonitrile was prepared. The solution was stored at $-20°$ C. when not in use. 2.5 ul of the stock monobromobimane solution was added to 20 ul of the protein solution in lysis buffer, so that the final concentration of monobromobimane was 22.2 mM. The mixture was vortexed briefly, then incubated at room temperature for 10 minutes. The reaction is complete after 10 minutes, but longer incubation times can be used (eg 30 minutes) so as to obtain optimum labelling, as reaction times may vary from protein to protein.

10 ul (approx 2 ug) of the reaction mixture was loaded onto the IEF-gel for analysis. Other volumes may be used if appropriate.

Isoelectric focusing

IEF gels (approx 0.75 mm×45 mm) were prepared, using the acrylamide solution essentially as reported previously (references 4 and 6), in disposable calibrated (44.7 ul) capillaries (Vitrex, Camlab, Cambridge, U.K.) which had been reduced in length to approximately 75 mm. The carrier ampholyte mixture consisted of Pharmalyte, pH rage 3-10 (Pharmacia)/Servalyte, pH range 3-10 (Serva)/Ampholine, pH range 5-7 (LKB)/Pharmalyte, pH range 4–6.5, (2:1:1:1, by vol.). The IEF apparatus made in our workshop was of circular design (15 cm diameter) consisting of separate upper and lower chambers. 12 IEF-gels were positioned evenly around the perimeter of the upper chamber, secured by rubber grommets, such that one end protruded approximately 2 cm into the upper chamber while the tip of the other end reached into the lower chamber. The anolyte solution consisted of 100 mM 2-(N-morpholino) ethane-sulphonic acid (MES) hydrochloride buffer, pH 2.92 at 20° C., containing 5% w/v sucrose, and the catholyte solution of 100 mM Na [bis(2-hydroxyethyl) iminotris(hydroxymethyl) methane] (Bis-Tris) buffer, pH 10.28 at 20° C., containing 5% w/v sucrose.

Prior to loading the sample the IEF-gels were overlayered with 15 ul 9M urea, 1.7% v/v Ampholine, pH range 9–11. Proteins were focused at 500V, 2000V and 2500V constant voltage for 200, 800 and 3000 Vh respectively. the outer surface of the capillary tubes and the top surface of the gels were washed with $H_2O$ prior to gel removal.

Extrusion of the mini IEF-gles was facilitated by using a capillary tube (20 ul, Drummond Microcap, Drummond Scientific Company, Broomall, Pa., USA.) plugged with Plasticene (modelling clay) as a piston. Alternatively, a 1 ml syringe containing $H_2O$ fitted with a Multiflex tip (Bioquote Limited), shortened suitably, can be used. Thus, the IEF gel, when required, could be loaded directly on to the second dimensional gel with relative ease.

If necessary the mini IEF gels could be stored frozen at −70° C. in plastic microcentrifuge tubes (2.0 ml, Bioquote Limited, Ilkely, U.K.). In this case, to allow correct orientation when loading the IEF gel on to the second dimensional gel at a later date, the extreme acidic end end of the IEF gel was marked with India Ink before being fully extruded into the microcentrifuge tube. The IEF gel may be stored and frozen in the absence of any liquid. When required the IEF gel may be allowed to thaw at room temperature briefly and then a small quantity of tank electrophoresis buffer added to allow the gel to be tipped

Second dimensional PAGE

Second dimensional PAGE was performed using the buffer system described by Laemmli (reference 8) and a cooled vertical dual slab unit apparatus from Hoefer Scientific Instruments (Newcastle under Lyme, U.K.) (model SE600) using pyrex glass plates, 179 mm (width)×82.5 mm (length) and 8 cm (nominal) clamps. Gradient gels (10–20% T; 2.6% C), 1.0 mm thick, were prepared with an overall dimension of 140 mm (width)×70 mm (height). Non-gradient gels may also be used. Prior to use the top surface was washed with $H_2O$ and overlayed with tank electrophoresis buffer. The mini IEF-gels were loaded on to the gradient slab gels such that 3 IEF-gels were positioned end to end along the top of each slab gel. The acidic end of each IEF-gel was to the left and a plastic gel spacer (0.5 mm thick, Hoefer) was used to push the IEF gels firmly but gently into position without causing then any damage. Agarose was not employed to seal the gels in place. Electrophoresis was carried out at +14° C. and at a constant current of 10 mA per gel for 15 minutes and then at 20 mA per gel until 30 min after the buffer front had reached the end of the gel (approx. 160 min in total). The buffer front was observed by its optical discontinuity in the gel.

Gel Imaging using the cooled CCD

Fluorescent gels were imaged electronically without being removed from their pyrex glass moulds using the Astromed (Cambridge, U.K.) 2200 Imaging System basically as described previously (reference 9). The gels were illuminated by visible light from a 50W tungsten-halogen lamp. The excitation and emission interference filters (Omega Optical Inc, Brattleboro, Vermont, USA) were 390DF70 and 480LP respectively. These filters had transmission maxima which corresponded approximately to the absorbance and emission maxima of the two fluorophore. The illumination was in the plane of the gel from the anodic edge using a fibre-optic light guide with the dimensions 0.5 mm×90 mm. The light guide was adjusted so that its aperture was aligned with the gel edge. The gel was placed so that it was as close as possible to, but without touching, the lightguide. During the viewing time the position of the gel, which was placed on a precision carriage, was altered with respect to the light guide by the computer system. When being viewed the gel remained stationary. The gel image was demagnified 5-fold by a lens with an aperture of f1.2. The CCD was cooled to approx. 218K by a Peltier cooler. Each gel was viewed in six sections and the images joined by the associated computer such that a composite image of the whole gel could be portrayed on the graphics display screen. The time for viewing each section of an individual gel was constant but could be varied from gel to gel. The time normally used was 60 seconds. The CCD response was directly proportional to the imaging time.

FIG. 2 is a photograph of the resulting CCD image obtained in this way. In FIG. 2, 3 IEF gels indicated by the white line across the top of the image were located end-to-end on the second dimensional gel, with the acidic end of each labelled A and the basic end of each labelled B.

REFERENCES

1. O'Farrell, P. H. (1975) J. Biol. Chem. 250, 4007–4021.
2. Finger, J. M. & Choo, K. H. (1981) Biochem. J. 193, 371–374.
3. Hames, B. D. (1990) in Gel Electrophoresis of Proteins: A Practical Approach (Hames, B. D. & Rickwood, P., Eds), 2nd edition pp. 67–68, Oxford University Press, Oxford.
4. Jackson, P., Urwin V. E. & Mackay, C. D. (1988) Electrophoresis, 9, 330–339.
5. Cornwall, G. A.+Chang, T.S.K. (1990) Journal of Andrology, Vol. 11, No: 2, 168–181.
6. Jackson, P., Urwin, V. E., Torrance, M. R. and Carmen, J. A. (1989) Electrophoresis 10, 456–463.
7. Bradford, M. M. (1976) Anal. Biochem. 72, 248–254
8. Laemmli, U. K. (1970) Nature 227, 680–685.
9. Jackson, P. (1990) Biochem. J. 270, 705–713.

I claim:

1. A method of separating or distinguishing proteins by isoelectric focusing, comprising fluorescently labelling proteins by reacting monobromobimane or monochlorobimane with free sulphydryl groups of the proteins, and subjecting the labelled proteins to isoelectric focusing.

2. A method according to claim 1, wherein labelling is effected by reacting protein in lysis buffer with monobromobimane or monochlorobimane added in solution in acetonitrile, by mixing and incubating at room temperature for between 2–60 minutes.

3. A method according to claim 1, wherein free sulphydryl groups are produced in proteins to be labelled by reduction of disulphide bridges.

4. A method according to claim 1, wherein the electrophoretic separations(s) are carried out on polyacrylamide gels.

5. A method according to claim 1, wherein the labelled proteins are viewed using an imaging system based on a cooled 2D charge coupled device.

6. A method of separating or distinguishing proteins by two dimensional electrophoresis, comprising fluorescently labelling proteins by reacting monobromobimane or monochlorobimane with free sulphydryl groups of the proteins, subjecting the labelled proteins to isoelectric focusing in a first dimension, then subjecting the proteins to gel electrophoresis in a second dimension.

7. A method according to claim 6, wherein the second dimension gel electrophoresis is carried out in the presence of sodium dodecyl sulphate.

8. A method according to claim 6, wherein labelling is effected by reacting protein in lysis buffer with monobromobimane or monochlorobimane added in solution in acetonitrile, by mixing and incubating at room temperature for between 2-60 minutes.

9. A method according to claim 6 wherein free sulphydryl groups are produced in proteins to be labelled by reduction of disulphide bridges.

10. A method according to claim 6 wherein the electrophoretic separation are carried out on polyacrylamide gels.

11. A method according to claim 6 wherein the labelled proteins are viewed using an imaging system based on a cooled 2D charge coupled device.

* * * * *